US010603391B2

(12) United States Patent
Mishkin et al.

(10) Patent No.: US 10,603,391 B2
(45) Date of Patent: Mar. 31, 2020

(54) STETHOSCOPE SANITIZING DEVICE

(71) Applicant: APOLLO RENAL THERAPEUTICS, LLC, Ocala, FL (US)

(72) Inventors: Gary Mishkin, Potomac, MD (US); Aslan Leo Riza, Sarasota, FL (US); Erkan Riza, Sarasota, FL (US); Robert Steinberg, Portsmouth, NH (US)

(73) Assignee: APOLLO RENAL THERAPEUTICS, LLC, Ocala, FL (US)

( * ) Notice: Subject to any disclaimer, the term of this patent is extended or adjusted under 35 U.S.C. 154(b) by 26 days.

(21) Appl. No.: 15/569,522

(22) PCT Filed: Apr. 26, 2016

(86) PCT No.: PCT/US2016/029292
§ 371 (c)(1),
(2) Date: Oct. 26, 2017

(87) PCT Pub. No.: WO2016/176168
PCT Pub. Date: Nov. 3, 2016

(65) Prior Publication Data
US 2018/0296709 A1 Oct. 18, 2018

Related U.S. Application Data

(60) Provisional application No. 62/153,149, filed on Apr. 27, 2015.

(51) Int. Cl.
*A61L 2/10* (2006.01)
*A61L 2/00* (2006.01)
(Continued)

(52) U.S. Cl.
CPC .............. *A61L 2/0047* (2013.01); *A61B 7/02* (2013.01); *A61B 90/70* (2016.02); *A61L 2/10* (2013.01); *A61L 2202/24* (2013.01)

(58) Field of Classification Search
CPC ......... A61L 2/10; A61L 2202/24; A61B 7/02; A61B 90/70
See application file for complete search history.

(56) References Cited

U.S. PATENT DOCUMENTS 7,705,325 B2    4/2010   Vestal
8,779,385 B2 *  7/2014   Noori ........................ A61L 2/10
                                                        250/455.11

(Continued)

FOREIGN PATENT DOCUMENTS

KR      101441078 B1      9/2014
WO      02/056920 A2      7/2002
WO      2013/068973 A2    5/2013

*Primary Examiner* — Timothy C Cleveland
(74) *Attorney, Agent, or Firm* — Browdy and Neimark, P.L.L.C.

(57) ABSTRACT

A sanitizing device for sanitizing a chestpiece of a stethoscope connected to at least one earpiece by a tube, the sanitizing device being composed of: a housing composed of two housing halves and a hinge assembly connecting the housing halves together to permit relative pivotal movement between the housing halves between a closed state in which the housing halves enclose a closed space, and an open state; and a source of sanitizing radiation disposed to irradiate the closed space. The housing is provided with an opening for receiving the tube; the opening is composed of two opening portions each formed in a respective housing half; and the hinge assembly is composed of two hinge portions each forming part of a respective housing half, the hinge portions being separable from one another to allow the chestpiece to be placed in the closed space.

17 Claims, 9 Drawing Sheets

(51) Int. Cl.
*A61B 90/70* (2016.01)
*A61B 7/02* (2006.01)

(56) References Cited

U.S. PATENT DOCUMENTS

| | | | |
|---|---|---|---|
| 8,795,438 B2* | 8/2014 | Rubin | A61L 2/28 134/56 R |
| 2002/0162972 A1 | 11/2002 | Pleet | |
| 2004/0155201 A1 | 8/2004 | Russel et al. | |
| 2005/0163653 A1 | 7/2005 | Crawford et al. | |
| 2006/0147339 A1 | 7/2006 | Hunter et al. | |
| 2008/0166384 A1 | 7/2008 | Jones | |
| 2009/0311149 A1 | 12/2009 | Freedgood | |
| 2010/0003175 A1 | 1/2010 | Gibson | |
| 2010/0266445 A1 | 10/2010 | Campagna | |
| 2010/0314553 A1 | 12/2010 | Yerby | |
| 2011/0020175 A1 | 1/2011 | Collard et al. | |
| 2012/0006995 A1 | 1/2012 | Greuel | |
| 2012/0051969 A1 | 3/2012 | Nahman et al. | |
| 2013/0004367 A1 | 1/2013 | Roberts | |
| 2014/0319374 A1 | 10/2014 | Chandler | |
| 2015/0359945 A1* | 12/2015 | Rosenblatt | A61B 42/00 424/404 |
| 2017/0182305 A1* | 6/2017 | Kermode | A61M 39/18 |

* cited by examiner

STETHOSCOPE SANITIZING DEVICE

BACKGROUND OF THE INVENTION

The present invention relates to devices for sanitizing stethoscope chestpieces. The sanitizing device according to the invention can be used to sanitize, or disinfect, the chestpiece of any type of stethoscope: acoustic; electronic; etc.

Acoustic stethoscopes operate on the transmission of sound from the chestpiece, via air-filled hollow tubes, to the listener's ears. The chestpiece usually consists of two sides that can be placed against the patient for sensing sound: a diaphragm (plastic disc); or a bell (hollow cup). If the diaphragm is placed against the patient, body sounds vibrate the diaphragm, creating acoustic pressure waves that travel up the tubing to the listener's ears. If the bell is placed against the patient, the vibrations of the skin directly produce acoustic pressure waves traveling up to the listener's ears. The bell transmits low frequency sounds, while the diaphragm transmits higher frequency sounds.

BRIEF SUMMARY OF THE INVENTION

The sanitizing device according to the invention is a stethoscope sanitizer that may be constructed to be carried by and, stored on, the stethoscope tube so as to be readily available to perform a sanitizing, or disinfecting, operation. The sanitizing device is preferably powered by a battery housed within the device, thus eliminating the need for external connections to the device. The battery, or batteries, may be rechargeable or replaceable.

According to a preferred embodiment of the invention, the sanitizer is composed of a two-piece housing, which may be of generally cylindrical form, the two pieces of the housing being connected together by a detachable, or permanent, hinge. At the hinge side of the housing there is provided a circular opening provided with an expandable foam rubber gasket. The gasket is preferably made of two parts, each carried by a respective housing piece. The opening is provided to receive a stethoscope tube, while the interior of the housing is provided to receive the stethoscope chestpiece. The gasket assures that, when the housing is closed the gasket will form a seal with the tube in order to isolate the interior of the sanitizer from the surrounding environment.

The upper side of the housing is provided with an electronic protection cover that may receive an on/off button.

Within the housing there are provided UV light sources, which may be LED's. LED's are selected that emit light in the UV-C wavelength range (100-280 nm), ideally between 250-280 nm. It is considered that the best disinfection is achieved at wavelengths in the range of 250-300 nm. The housing also contains a battery compartment and a timer indicating that the sanitizer is in operation and when the sanitization process has been completed.

The electronic protection cover is provided with an indicator which may emit a first color when the sanitizer is in operation and a second color when the sanitizing process has been completed.

When the sanitizer is not in use, it may be slid along the tube away from the chestpiece, with the housing slightly open. Thus, the sanitizer will be out of the way and not interfere with use of the stethoscope.

When a sanitization process is to be performed, the sanitizer is slid along the tube to a position surrounding the chestpiece. The housing pieces are then closed and the on/off button is operated to initiate a sanitization process. Alternatively, the device may also turn on automatically when the pieces are closed.

For the sanitizing operation, either the diaphragm or the bell of the chestpiece may be oriented to face the UV light sources.

If the sanitizer is provided with a rechargeable battery, the housing may contain a charging port, such as a micro USB port for connection of the battery to a charging cable.

The bottom of the housing is provided with a circular array of air vents that provide heat dissipation. These vents are optional and not needed if the heat generated is found to be sufficiently low. They are required if the device were to generate heat that could be dangerous to the user or to the circuitry.

The material of the housing of the device may contain an antimicrobial additive, which could be a silver based resin, or preferably an antimicrobial resin, that is added during production to give the device long term antimicrobial efficacy. Biosafe® Silane additive marketed by the RTP Company of Winona, Minn., is one example. This product consists of 84% 3-(trihydroxysilyl) propyldimethyloctadecyl ammonium chloride as the active ingredient and 10% inert ingredients, While UV radiation will kill everything inside the device, the outside of the device may still carry harmful microbes. A user will touch the outside of the device, then touch parts of the stethoscope. If the housing contains an antimicrobial additive, the risk of such cross contamination is reduced.

The housing is equipped with a hinge system that allows the user to put the device onto the tube of the stethoscope without the need to remove the chestpiece (diaphragm/bell) or to use tools. This hinge also results in a wider opening on the part of the tube when the device is open, facilitating the sliding of the device up the tube or down over the diaphragm.

Alternatively, the two halves may be permanently attached at the hinge, which would require the user to remove the chestpiece, slide the device on the tube and reattach the chest piece. The sanitizing device will continue to function as described above.

The inside walls of the device may be reflective to UVC radiation to increase the chestpiece surface area that is exposed and sanitized. This can be achieved by coating the interior walls of the housing with a reflective material such as a thin coat of spray metal or by painting with a product such as UVC Max, marketed by UltraViolet Devices, Inc., which can reflect the UVC radiation. Also, the inside walls of the housing need not be smooth. By giving the inside walls a corrugated form, the radiation can be reflected to get around potential shadows from the stethoscope.

The LED's preferably have a field of emmitance that is as much as 120 degrees. The LED's are preferably placed so that the diaphragm gets the most exposure. In addition, some LED light goes around the diaphragm, impinges on the reflective interior walls of the housing and is reflected to other parts of the stethoscope. This gives a more complete sanitization of the stethoscope chestpiece.

In order to allow maximum exposure to the diaphragm of the stethoscope from the UV LED's, the diaphragm can be elevated to allow the spread of the UV light (120 degrees). For this application, a distance of approximately 0.3 inches provides good exposure. The more LED's used, the closer the diaphragm can be to get full exposure.

One possible solution is to have one or more posts, or a support surface, to prop up the distal end of the diaphragm while in the device. Alternatively, there are several materials that permit the passage of UV light, such as quartz, ethylene vinyl acetate, polyolefins and fluorinated ethylene propylene. Thinner pieces permit better penetration of the UV light. A ring or feet (approximately 0.3 inches in height, depending on the number and spacing of LED's), with a cover of material that permits UVC light penetration can be used so the diaphragm rests on the material and ring, elevated above the LED's. The LED light passes through the material and sanitizes the surface of the diaphragm. The material and ring may be removable so it can be cleaned and/or replaced, as needed.

Finally, it is preferable for the hospital or clinic to track use of the stethoscope device. This data can easily be tracked by the device and then downloaded to a computer, via the mini USB port (same as used to charge the device). Alternatively, a bluetooth or WIFI capable device can sync automatically (when formatted properly) with the hospital's or clinic's IT system. This would, in real time, track the use of the device to aid in assessment of compliance.

DETAILED DESCRIPTION OF THE INVENTION

Figure 1:
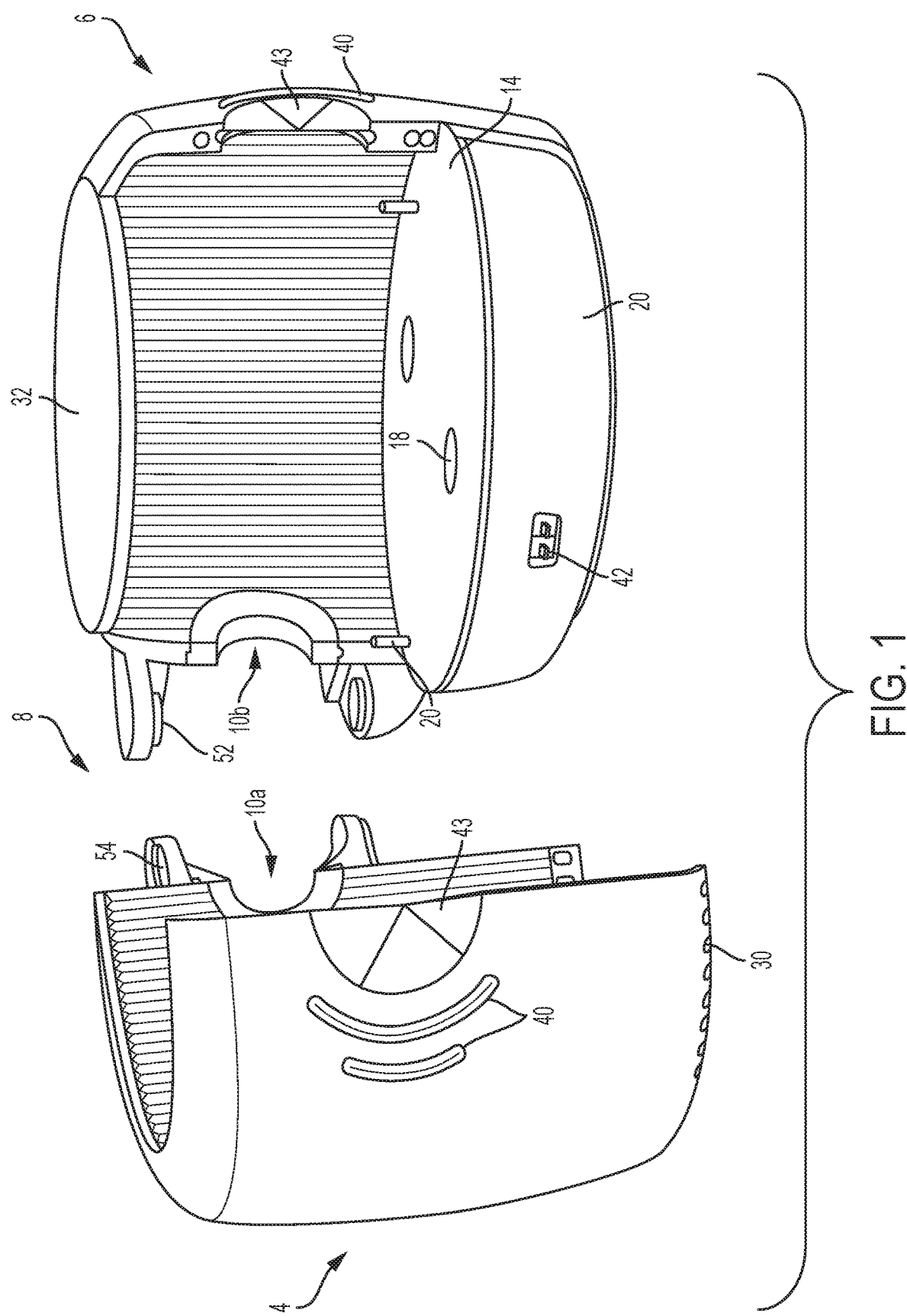
FIG. 1 is a perspective view of a first embodiment of a sanitizing device according to the invention, with the two parts of a housing separated from one another.

FIG. 1 shows a first embodiment of the housing for a sanitizing device according to the invention. The housing is made in two parts 4 and 6 coupled together by a detachable hinge assembly 8. Each housing part is provided, in the vicinity of hinge assembly 8, with a respective half, 10a, 10b, of an opening that will have a circular form when the housing is closed. Opening halves 10a, 10b are provided with flexible seals that assure a light-tight coupling between the opening and a stethoscope tube 44 (shown in FIG. 2).

The interior of the housing is divided by a plate 14 into an upper portion, where the interior walls of the housing are vertically corrugated, and a lower portion that will contain circuit components of the device. Plate 14 is provided with two UV LED's 18, although one, or more than two, LED's may be provided. Plate 14 is also provided with two posts 20, the purpose of which will be described below in the description of FIGS. 8a and 8b.

Figure 4:
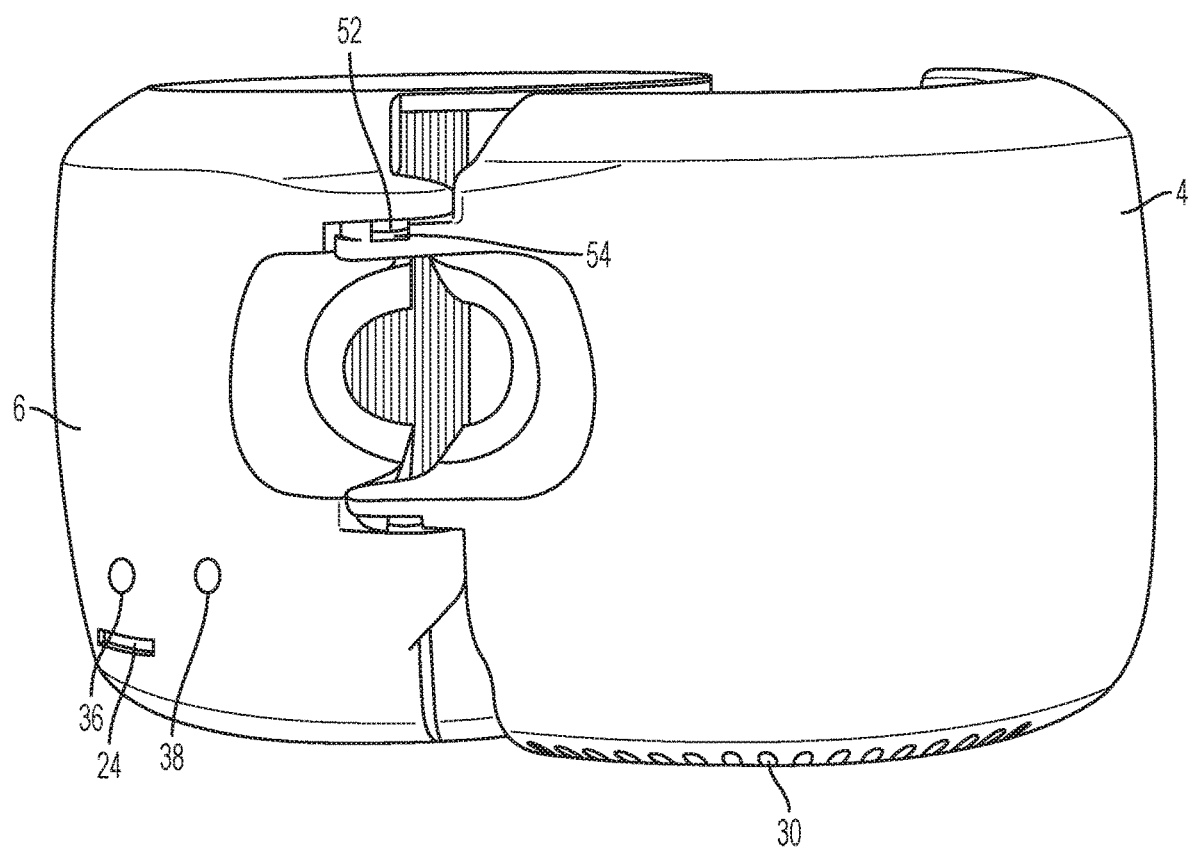
FIG. 4 is a perspective view showing a device according to the invention from the side opposite of that of FIG. 1.

Within the housing, plate 14 covers a cylindrical interior housing in which the circuit components are installed. As shown in FIG. 4, housing part 6 carries a port 24, such as a USB port, for connection of a battery charging cable, as well as an indicator light 36 and an on/off button 38. Indicator light 36 may be a simple two-color LED (red/green).

The bottom of each housing part is provided with optional air vents 30, the purpose of which has been described above.

The top of the housing is closed in a light-tight manner by a cover plate 32.

Each housing part 4, 6 is provided with a portion of a latch assembly for maintaining the housing in a closed state. The latch assembly may be a magnetic assembly constituted by magnets 40 on each housing part and cooperates with a sensor, or case switch, 42 composed of two contacts that are bridged by a conductive contact piece (not visible) in the inner wall of housing part 4 when the housing is in a fully closed state to activate the circuit. Magnets 40 may surround opening halves in housing parts 4, 6, provided with flexible diaphragms 43 that enable the housing to be at least partially closed on tube 44 when the device is not in use. Flexible diaphragms 43 also prevent the light from escaping when in the fully closed state and LEDs are on. However, it is presently preferred to use a mechanical latch assembly of the type that clicks closed, an example of which will be described below with reference to FIG. 5.

Figure 2:
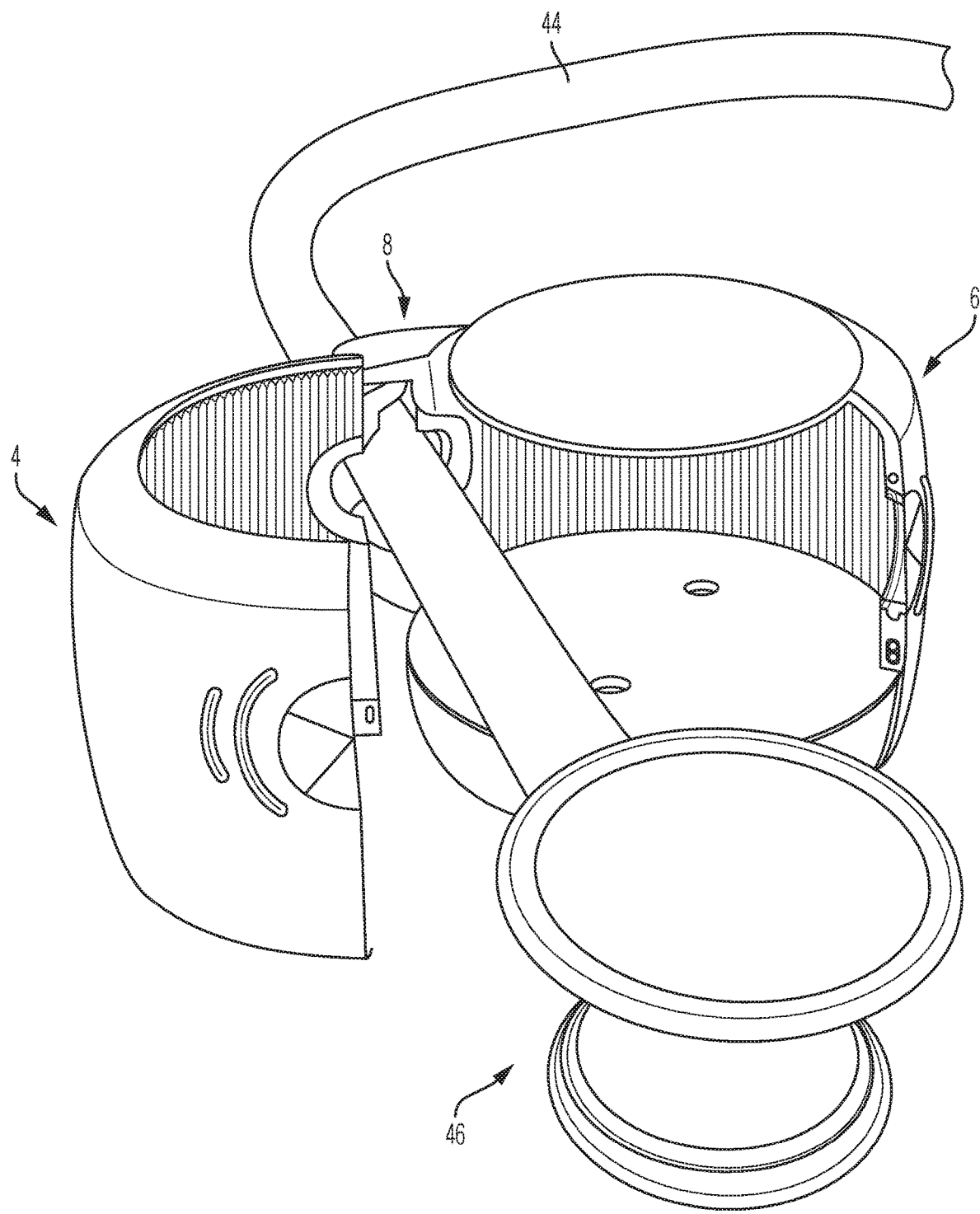
FIG. 2 is a perspective view of the device in FIG. 1, with the two parts of the housing assembled together and the housing in an open state.

FIG. 2 is a perspective view showing the device of FIG. 1 with the parts of hinge assembly 8 joined together to provide a pivotable connection between housing parts 4 and 6. A stethoscope tube 44 extends through opening 10a, 10b so that the stethoscope chestpiece 46 can be introduced into housing 4, 6.

In order to allow stethoscope tube 44 to pass through opening 10a, 10b, the parts of hinge assembly 8 are separated and then connected back together after being placed around tube 44. Thus, when the device is not in use, it can remain in place on tube 44 at a location spaced from chestpiece 46.

Figure 3:
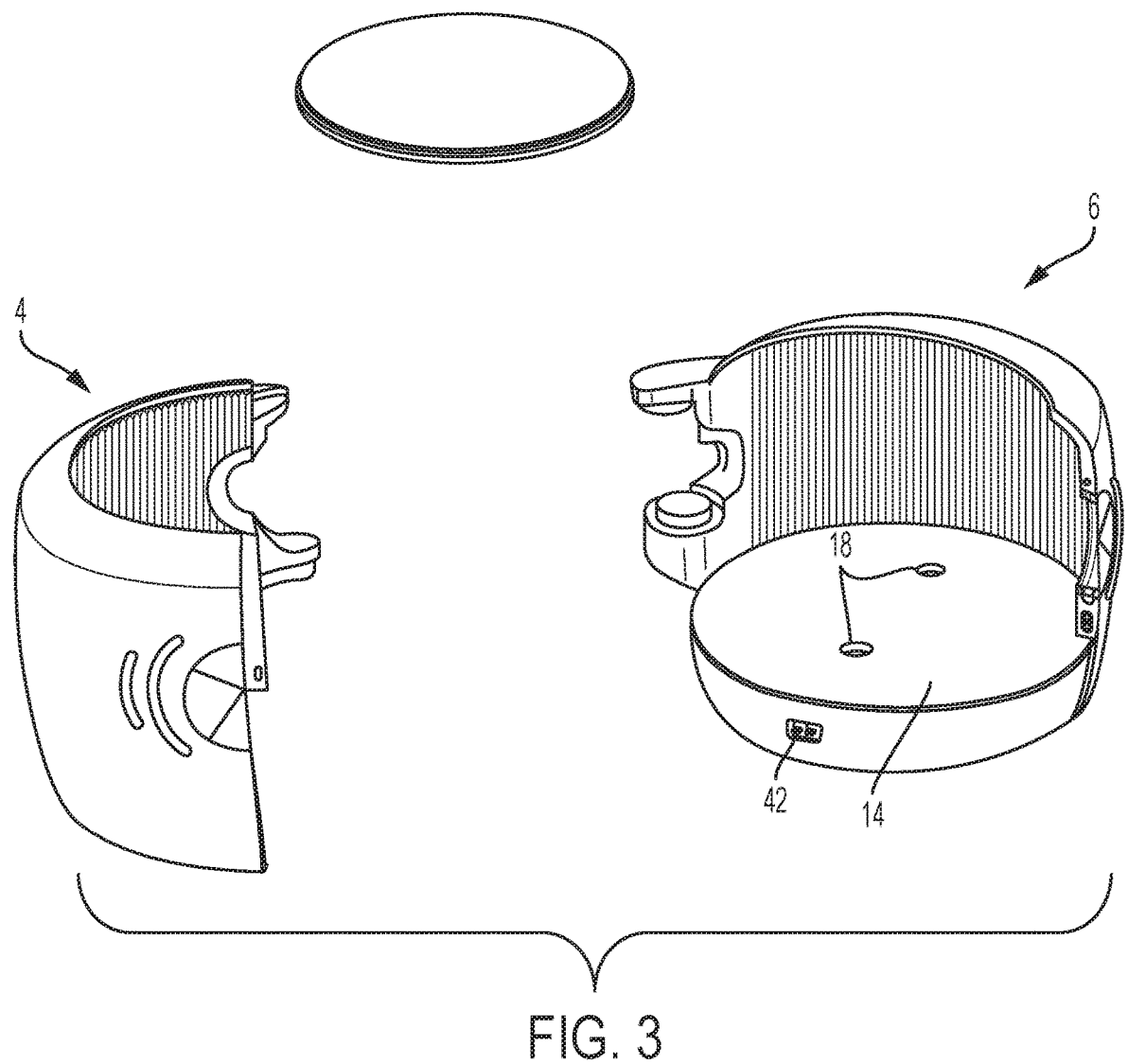
FIG. 3 is an exploded view showing various components of the embodiment of FIG. 1.

FIG. 3 is a further perspective view showing housing parts 4, 6 of the embodiment of FIGS. 1 and 2 separated from one another.

FIG. 4 is a perspective view of the hinge side of the housing of a device according to the invention.

Housing part 6 is provided with indicator 36 that will exhibit a change in color dependent upon the operating state (Green for UV LED's off, ok to open to Use, Red for UV LED's on, do not open), as well as port 24 and on/off button 38. Indicator 36 is located on the outside lower section opposite sensor 42 (FIG. 3).

The hinge parts shown in FIG. 4 may be temporarily separable, or disconnectable, from one another, or may be permanently connected together.

Each hinge part has two arms and each arm of one hinge part is provided with a respective pin, or button, 52, while each arm of the other hinge part is provided with a recess 54 into which a respective pin 52 is fitted. Pins 52 and recesses 54 thus form the hinge mechanism. In the case that the hinge parts are separable, at least one of the arms carrying a pin 52 is sufficiently flexible to allow the hinge parts to be separated from one another when desired. In the case where the hinge parts are permanently connected together, the arms will be essentially rigid, or otherwise constructed to prevent separation.

The sanitizing device is constructed so that the upper portion of the interior of the housing is light-tight when the housing is closed.

This latch mechanism may be constructed to have a fully closed state which engages sensor contacts and cycles the LEDs ON, and a partially closed state for when the device is stored on tube 44. In the partially closed state, the sensor contacts are not bridged so the device does not cycle ON.

Figure 5:
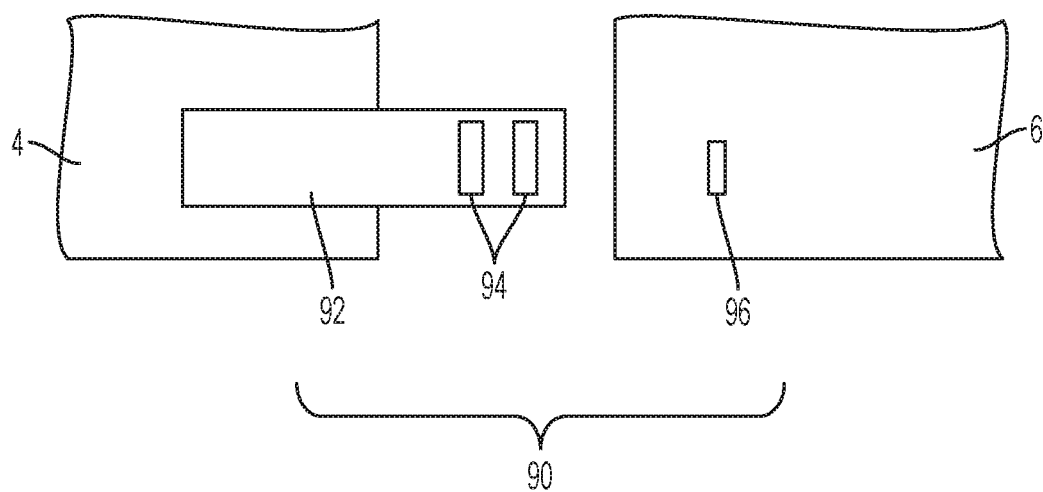
FIG. 5 is a detail view of the device of FIG. 1 with a modified latch assembly

FIG. 5 is a detail view showing such a latch assembly 90. This assembly is composed of a strip 92 secured at its left-hand end to housing part 4 and provided at its right-hand end with two openings 94. The assembly further includes a projection 96 configured to engage in either opening 94, depending on whether the device is to be fully closed or partially closed, as those states were described above.

Figure 6:
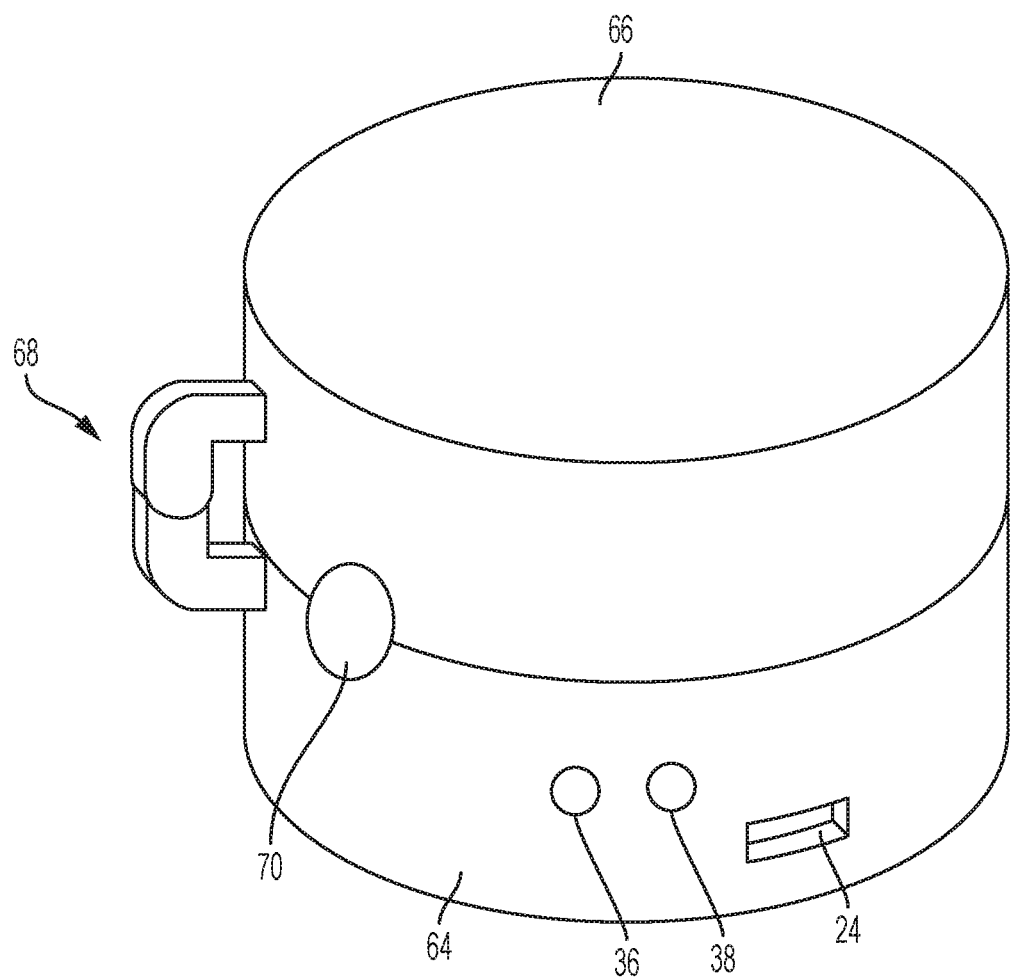
FIG. 6 is a perspective view of a second embodiment of a device according to the invention.

FIG. 6 shows an alternative embodiment of the invention in which each of two housing parts 64 and 66 is cylindrical and the two parts meet along a plane that is parallel to the top and bottom surfaces of the housing. Housing parts 64 and 66 are connected together by a hinge assembly 68. The housing parts 64 and 66 are formed to present respective portions of an opening 70 for passage of the stethoscope tube. Opening 70 can be located anywhere along the periphery of the device, as long as it is clear of hinge assembly 68.

Apart from the features of the alternative embodiment shown in FIG. 6 and described above, other features of this embodiment are essentially identical to those of the embodiment of FIGS. 1-4, particularly with regard to the provision of the sanitizing light sources, the control circuitry, the on/off button, the indicator light, plate 14 and the air vents.

Figure 7:
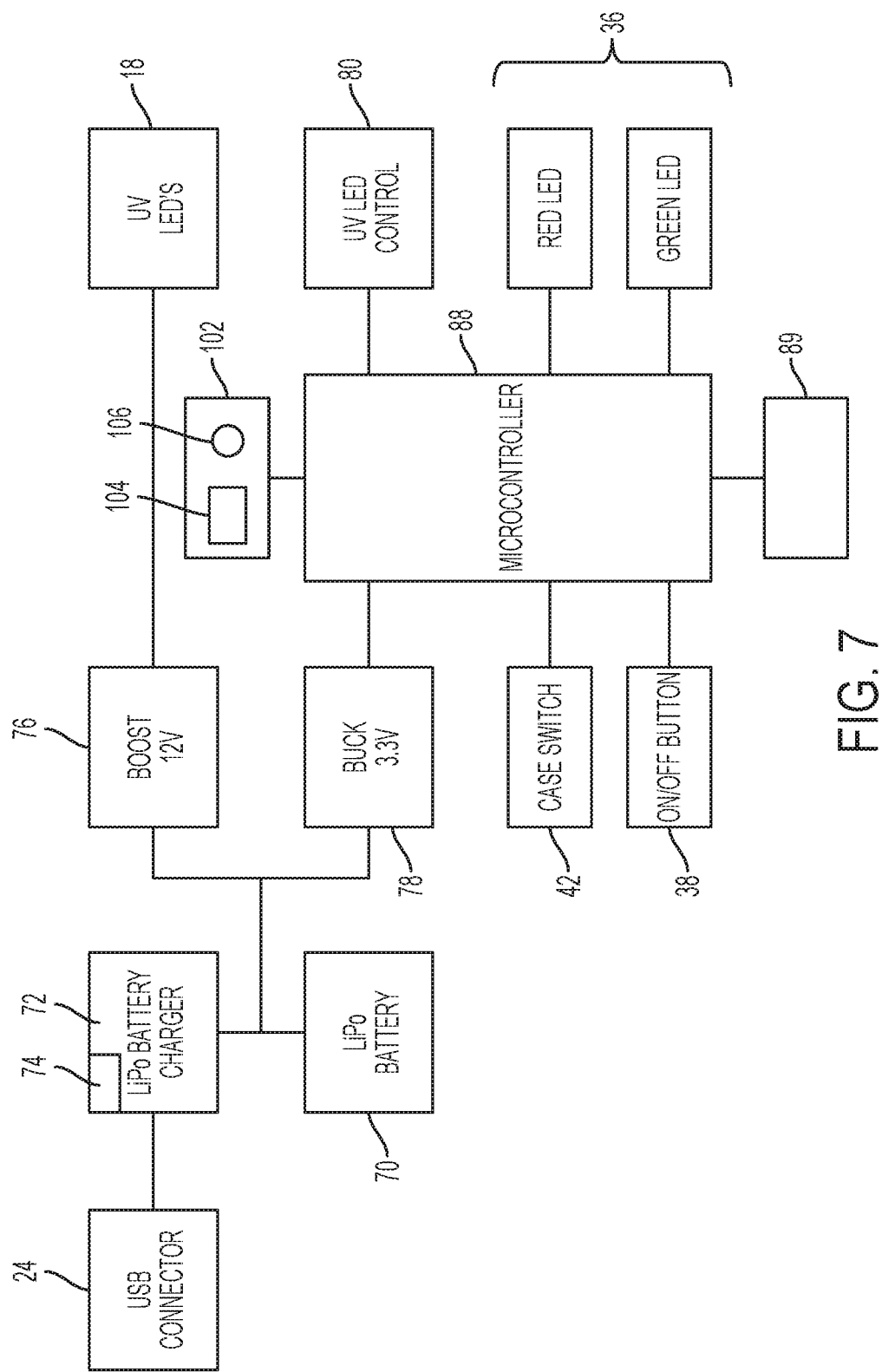
FIG. 7 is a block diagram of a circuit for operating the device according to the invention.

FIG. 7 is a block diagram of a basic circuit that can be employed to control the operation of the sanitizing device. USB port 24 is connected to a battery 70 via a battery charger 72, which may be provided with a conventional charging indicator light 74. Battery 70 is coupled to two converters, which may be a 12V boost converter 76 and a 3.3V buck converter 78. Boost converter 76 is connected to supply operating power to UV LED's 18, controlled by a LED control 80. Converter 78 acts to supply operating power to a microcontroller 88.

There is also provided the case switch 42 that is activated when the housing is closed, i.e., when the portions of latch assembly 40 are in contact with one another.

Indicator 36 is equipped with a red LED and a green LED

The circuit may also be provided with a transmitter 89, connected to be operated by microcontroller 88, that is responsive to operation of button 38 to emit a signal to a central facility monitor each time the device is placed into operation. This allows the number of uses of the device to be monitored at the central facility. Transmitter 89 may also be controlled to emit a signal each time the device is turned off. This allows the central facility to also monitor the total usage time of the device. Transmitter 89 may be programmed or configured to include in the emitted signal an identification of the device.

In addition, or as an alternative, to transmitter 89, the circuit may be provided with a memory, or data storage, unit 102 connected to be operated by microcontroller 88 in response to on and off operations of button 38. Unit 102 may include a display 104 and a reset button 106, Memory device 88, will record the date, time and frequency of use, and the number of uses and cumulative time of use from a starting time determined by operation of a reset switch, or button 106. The resulting data may be sent to a computer via transmitter 89 or the miniUSB port 24. This may be used to track frequency of use and compliance.

Components 36, 38, 42, 78, 80 and 89 are all connected to microcontroller 88 that, according to one preferred embodiment, is configured, or programmed, to act as a timer.

When button 38 is placed in the on state, and case switch 42 is activated, microcontroller 88 provides a signal to control 80 to activate LED's 18 and to turn on the red LED of indicator 36. At the end of a period of time set in microcontroller 88, the microcontroller signals control 80 to turn off LED's 18 and the red LED of indicator 36, and turn on the green LED of indicator 36. The housing may then be opened and slid along tube 44 to allow chestpiece 46 to be removed from the device.

As an alternative to the circuitry shown in FIG. 7, a simplified operating circuit can be provided in which button 38 is directly connected to control 80 to manually turn LED's 18 on and off to perform a sanitizing operation for a time determined by the user, and an interlock may be provided to enable control 80 to operate only when case switch 42 is closed.

LED's 18 are preferably of the instant on and off type so if the user needs to use the stethoscope before a sanitizing operation is completed, opening of the device will immediately turn LED's 18 off.

In practical implementations of the invention, battery 70 is rechargeable, and the device is constructed to provide at least 60 minutes of operability (LEDs ON) per battery charge.

Ideal cycle times range between 30 seconds to 2 minutes to achieve at least a 3 log reduction in common organisms such as MRSA and VRE. Longer times can be delivered if more resistant organisms are to be targeted or an outbreak is suspected. Similarly, more LEDs can be used to achieve the same antimicrobial activity in a shorter exposure time, or greater activity in the same exposure time. Shorter times can be used, if lower activity is required.

Figure 8A:
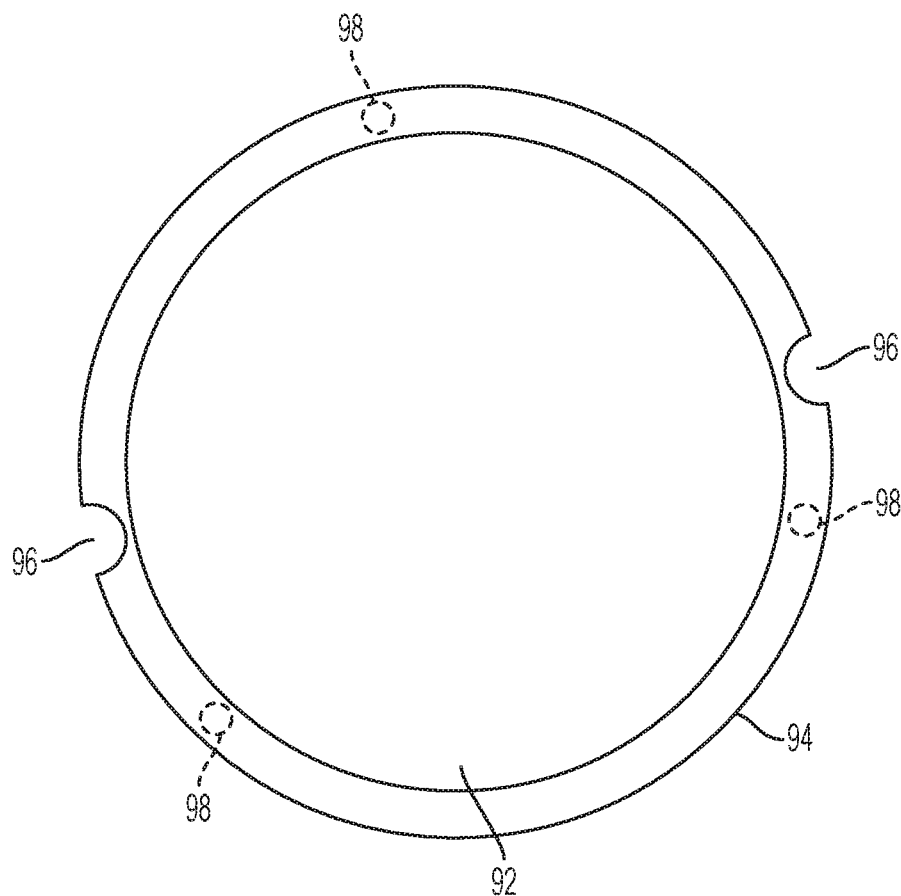
FIGS. 8A and 8B are, respectively, a top plan view and a side view of an accessory for supporting a chestpiece at a height to assure an improved sanitizing treatment.
Figure 8B:
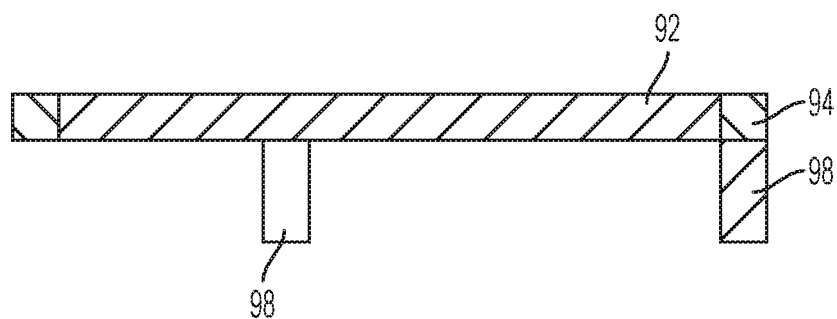

FIGS. 8a and 8b show an accessory in the form of a stand that will be placed on plate 14 to support a chestpiece. The purpose of this stand is to maintain the chestpiece component that is being sanitized at an optimum distance above LED's 18 to assure that the entire surface of the chestpiece component is irradiated. It is presently considered that a distance of about 0.3 inch from the LED's will provide the desired coverage, at least when three LED's are provided.

The stand is composed of a circular plate 92 carried by a frame 94 having two recesses 96 in its outer surface. Frame 94 is supported on three legs 98 dimensioned to provide the desired distance between the LED's and the chestpiece component. Frame 94 may also be a 360° ring, which snaps into a holder on housing 6. Plate 92 is of a material that is substantially transparent to the LED radiation, such as FEP, quartz, etc. In order to properly position, and retain, the stand on plate 14 (FIG. 1), posts 20 are engaged in recesses 96.

Figure 9:
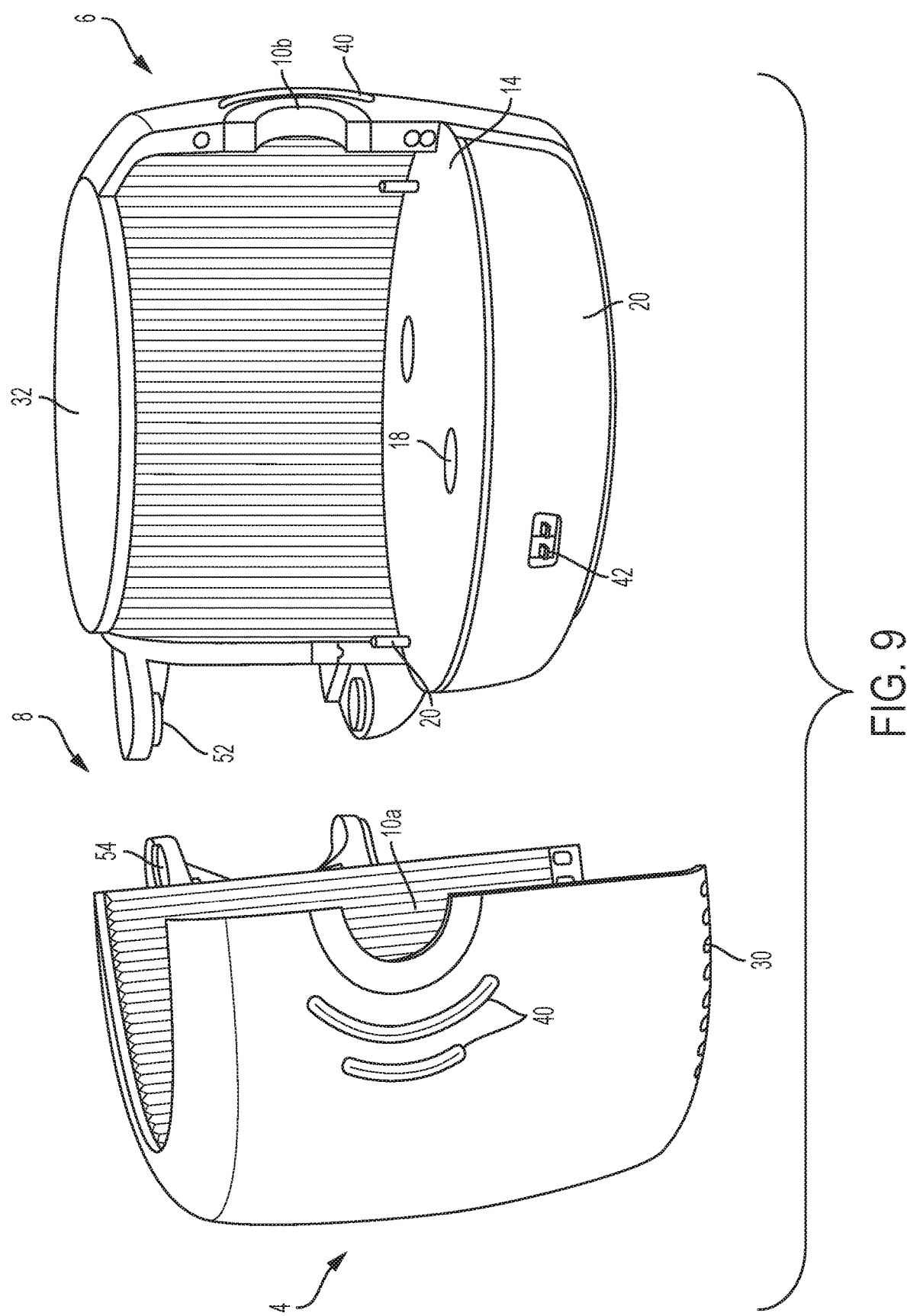
FIG. 9 is a view similar to that of FIG. 1 showing a second embodiment of a device according to the invention.

FIG. 9 shows a second embodiment of a device according to the invention, which will not be stored on the stethoscope tube, but will be placed around the chestpiece when needed. The only difference from the embodiment of FIGS. 1-4 are that opening 10a, 10b is moved to a location diametrically opposite hinge assembly 52, 54 and diaphragm 43 is eliminated. The opening 10a and 10b may be have a flexible seal or a flexible diaphragm, both preventing light from escaping when the LEDs are activated, Although exemplary embodiments of the present invention have been described, this should not be construed to limit the scope of the appended claims. Those skilled in the art will understand that various modifications may be made to the described embodiment. Moreover, to those skilled in the various arts, the invention itself a described herein will suggest solutions to other tasks and adaptations for other applications. It is therefore desired that the present embodiments be considered in all respects as illustrative and not restrictive, reference being made to appended claims rather than the foregoing description to indicate the scope of the invention.

What is claimed is:

1. A sanitizing device for sanitizing a chestpiece of a stethoscope, the chestpiece being connected to at least one earpiece by a stethoscope tube having a generally circular cross section, and the chestpiece having at least one sensing element, said sanitizing device comprising:
a housing composed of two housing halves and a hinge assembly connecting said housing halves together to permit relative pivotal movement between said housing halves between a closed state in which said housing halves enclose a closed space, and an open state; and
a source of sanitizing radiation disposed to irradiate said closed space, wherein:
said housing is provided with an opening for receiving the stethoscope tube;
said opening is composed of two opening portions each formed in a respective housing half, said opening portions being separated from one another when said housing is in the open state; and
said housing has a hinge side at which said hinge assembly is disposed, said hinge assembly is composed of two hinge portions each forming part of a respective housing half, and said opening is located at said hinge side of said housing and said opening is located between said hinge portions; and
said opening is constructed to form a substantially light-tight coupling between said opening and the stethoscope tube when said housing is in the closed state and the stethoscope tube is extending through said opening, wherein said opening has a circular form when said housing is in the closed state.

2. The sanitizing device of claim 1, wherein said hinge portions are separable from one another to allow the chestpiece to be placed between said housing halves, with the stethoscope tube between said hinge portions, when said housing halves are in the open state.

3. The sanitizing device of claim 1, wherein said source of sanitizing radiation comprises at least one source of UVC radiation.

4. The sanitizing device of claim 3, wherein said source of UVC radiation is at least one LED.

5. The sanitizing device of claim 3, wherein said source of sanitizing radiation further comprises a timer connected and operative to control the time during which the source of UVC radiation operates.

6. The sanitizing device of claim 2, wherein said housing is made of a material containing an antimicrobial additive.

7. The sanitizing device of claim 1, further comprising a battery connected for powering said source of sanitizing radiation.

8. The sanitizing device of claim 7, wherein said battery is rechargeable.

9. The sanitizing device of claim 2, further comprising a second opening in a portion of said housing that is diametrically opposite to said hinge assembly, said second opening being constructed to prevent light from escaping from said closed space when said housing is in the closed state.

10. The sanitizing device of claim 1, wherein said hinge portions are permanently and pivotably connected together to allow the stethoscope tube to be inserted through said opening when the chestpiece is temporarily removed from the stethoscope tube.

11. The sanitizing device of claim 10, wherein said housing is made of a material containing an antimicrobial additive.

12. The sanitizing device of claim 1, further comprising a transmitter operative to broadcast a signal each time said device is placed into operation.

13. The sanitizing device of claim 1, further comprising:
a microcontroller; and a data recording, or storage, unit connected to be controlled by said microcontroller to store data representing at least one of: the frequency of use; the date of each use; and the time of each use of said device.

14. The sanitizing device of claim 1, further comprising a second opening in a portion of said housing that is diametrically opposite to said hinge assembly, said second opening being constructed to prevent light from escaping from said closed space when said housing is in the closed state.

15. The sanitizing device of claim 1, further comprising a support member arranged to be placed in said housing to cause the at least one sensing element of the chestpiece to face said source of sanitizing radiation and to be maintained at a distance from said source of sanitizing radiation, said distance being selected to assure that the entire surface of the at least one sensing element that faces said source of sanitizing radiation is irradiated.

16. A method of using the device of claim 1, comprising:
placing said housing halves in the open state;
placing said opening portions around the stethoscope tube;
placing said housing halves in the closed state with the chestpiece in said closed space; and
activating said source of sanitizing radiation for a time sufficient to sanitize said chestpiece.

17. The method of claim 16, wherein said placing said housing halves in the open state comprises separating said hinge portions from one another and said placing said housing halves in the closed state comprises reconnecting said hinge portions together.

* * * * *